(12) United States Patent
Stessman

(10) Patent No.: US 7,039,464 B2
(45) Date of Patent: May 2, 2006

(54) VOLTAGE INDEPENDENT MEASUREMENT APPARATUS, SYSTEM, AND METHOD

(75) Inventor: Nicholas J. Stessman, Minneapolis, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 562 days.

(21) Appl. No.: 10/314,874

(22) Filed: Dec. 9, 2002

(65) Prior Publication Data

US 2004/0111125 A1    Jun. 10, 2004

(51) Int. Cl.
*A61N 1/378* (2006.01)

(52) U.S. Cl. .......................... 607/27; 607/28; 341/141; 341/165

(58) Field of Classification Search ................. 607/27, 607/28; 608/27
See application file for complete search history.

(56) References Cited

U.S. PATENT DOCUMENTS

| | | | | |
|---|---|---|---|---|
| 5,137,020 A | * | 8/1992 | Wayne et al. ................. | 607/29 |
| 5,507,785 A | * | 4/1996 | Deno ........................... | 607/24 |
| 5,722,997 A | * | 3/1998 | Nedungadi et al. ........... | 607/28 |
| 5,741,311 A | * | 4/1998 | Mc Venes et al. ............ | 607/28 |
| H1929 H | | 12/2000 | Citak .......................... | 607/28 |

\* cited by examiner

*Primary Examiner*—Carl Layno
*Assistant Examiner*—Shevon Johnson
(74) *Attorney, Agent, or Firm*—Schwegman, Lundberg, Woessner & Kluth, P.A.

(57) ABSTRACT

A cardiac rhythm management apparatus may include a monitored energy source, a reference energy source, and a measurement module. The monitored source provides an initial pacing amplitude voltage and a pacing droop voltage, while the reference source provides a substantially fixed reference voltage. The measurement module, coupled to the monitored source and the reference source, provides a measurement related to the lead impedance associated with the rhythm management apparatus that is substantially independent of the reference voltage. Thus, a system may include the apparatus coupled to a lead wire. An article may cause a machine to implement a method which operates to determine a ratio of the actual initial pacing amplitude voltage to the actual pacing droop voltage.

16 Claims, 4 Drawing Sheets

VOLTAGE INDEPENDENT MEASUREMENT APPARATUS, SYSTEM, AND METHOD

TECHNICAL FIELD

Embodiments of the invention relate generally to cardiac rhythm management apparatus, systems, and methods. More particularly, embodiments of the invention relate to measurement apparatus, systems, and methods which can be used to determine various characteristics of cardiac pacing devices and their associated circuitry, including, for example, lead impedance measurement.

BACKGROUND

One task that arises in the use of cardiac rhythm management devices, including pacemakers, resides in the determination of lead impedance, that is, the effective resistance of the lead wire coupling the cardiac rhythm management device to the heart via electrodes within the heart. The measured value of lead impedance can provide useful information, such as enabling the estimation of remaining battery life, and data concerning the condition of lead wires For example, a relatively low lead impedance value may indicate a short circuit between the pacing electrodes. A relatively high lead impedance value may indicate an open circuit such as, for example, what might result from a lead wire that has become disconnected from the cardiac rhythm management device. To ensure effective pacing therapy is continuously available, each of these defective lead wire conditions must be detected and remedied as quickly as possible.

It is possible to calculate lead impedance based on a measurement of the voltage droop from a capacitively coupled pacing pulse delivered to the heart. Thus, traditionally, lead impedance measurements have been obtained by using a droop amplifier to measure the droop voltage, or a portion of the droop voltage, which appears across the pacing supply capacitor during delivery of a pacing pulse. In currently available products, the droop amplifier output is digitized by an analog-to-digital (A/D) converter, and the resulting value is transformed into an impedance value using a logarithmic function or a look-up table.

Different conditions surrounding the cardiac rhythm management device may require the use of different initial pacing voltage amplitudes. However, to accurately measure the lead impedance and compensate for changes in amplitude, either the gain of the droop amplifier must be adjusted, or the function/look-up table entries must be redefined. The first option is often chosen, since it may also be desirable to adjust the gain of the droop amplifier to allow full utilization of the A/D converter's dynamic range. However, choosing to adjust the droop amplifier gain often means that a different gain value will be needed for measuring the lead impedance at each different pacing voltage amplitude. Additional software, and/or hardware circuitry may be required to provide the necessary gain adjustment. Further, adjusting the gain may introduce inconsistency into the impedance measurement as the pacing voltage amplitude varies. Thus, there is a need in the art to measure lead impedance in a manner which is substantially independent of the initial pacing voltage amplitude.

SUMMARY

The apparatus, systems, and methods described herein provide a simplified approach to voltage-independent lead impedance measurement. The essence of the approach involves generating a ratio of an initial pacing voltage to a pacing droop voltage by balancing accumulated charges. In this discussion, the actual initial pacing voltage may be defined as the initial voltage on the pacing supply capacitor prior to pace delivery, and the actual pacing droop voltage may be defined as the difference between the initial pacing supply capacitor voltage (prior to pace delivery) and the final pacing supply capacitor voltage (at the end of the pace delivery). In addition, the referenced initial pacing voltage may be defined as the superposition of the actual initial pacing voltage around a reference indication, and the referenced pacing droop voltage may be defined as the as the superposition of the actual pacing droop voltage around a reference indication. The purpose of the reference indication is discussed below.

An apparatus according to various embodiments of the invention includes a monitored energy source (e.g., a pacing supply capacitor) that provides an actual initial pacing voltage and an actual pacing droop voltage. An optional attenuator, a reference energy source (e.g., a stable voltage source), and a measurement module are also included. The optional attenuator may be used to attenuate the actual initial pacing voltage (and possibly the actual pacing droop voltage) in order to make full utilization of the A/D converter's dynamic range and/or to accommodate the constraints of analog processing circuitry. The purpose of the reference energy source is to provide a convenient operating point, or bias, around which the analog signals can be processed within the measurement module. The measurement module can sample the actual initial pacing voltage and the actual pacing droop voltage, and can respectively convert these voltages into a referenced initial pacing voltage and a referenced pacing droop voltage for analog processing within the measurement module. By sampling the actual initial pacing voltage to accumulate a charge, and then balancing this accumulated charge against a charge proportional to the actual pacing droop voltage, a ratio of the actual initial pacing voltage to the actual pacing droop voltage, substantially independent of the reference indication, can be provided. Sampling may be accomplished using a plurality of capacitors arranged in a successive approximation configuration, such as might be used in a successive approximation A/D converter.

A system according to various embodiments of the invention includes the apparatus coupled to a lead wire. The system may further include a pacing voltage generator coupled to a pacing supply capacitor, and an attenuator.

A method according to various embodiments of the invention includes determining a ratio of the actual initial pacing voltage to the actual pacing droop voltage, perhaps by balancing accumulated charges, as noted previously. The ratio can be determined in a manner which is substantially independent of the reference indication. As will be demonstrated shortly, this ratio can be used to derive the pace output impedance value.

This summary is intended to provide an exemplary overview of the subject matter further described hereinbelow. It is not intended to provide an exhaustive or exclusive explanation of various embodiments of the invention. The Detailed Description that follows is included to provide further information about such embodiments.

DETAILED DESCRIPTION

Figure 1:
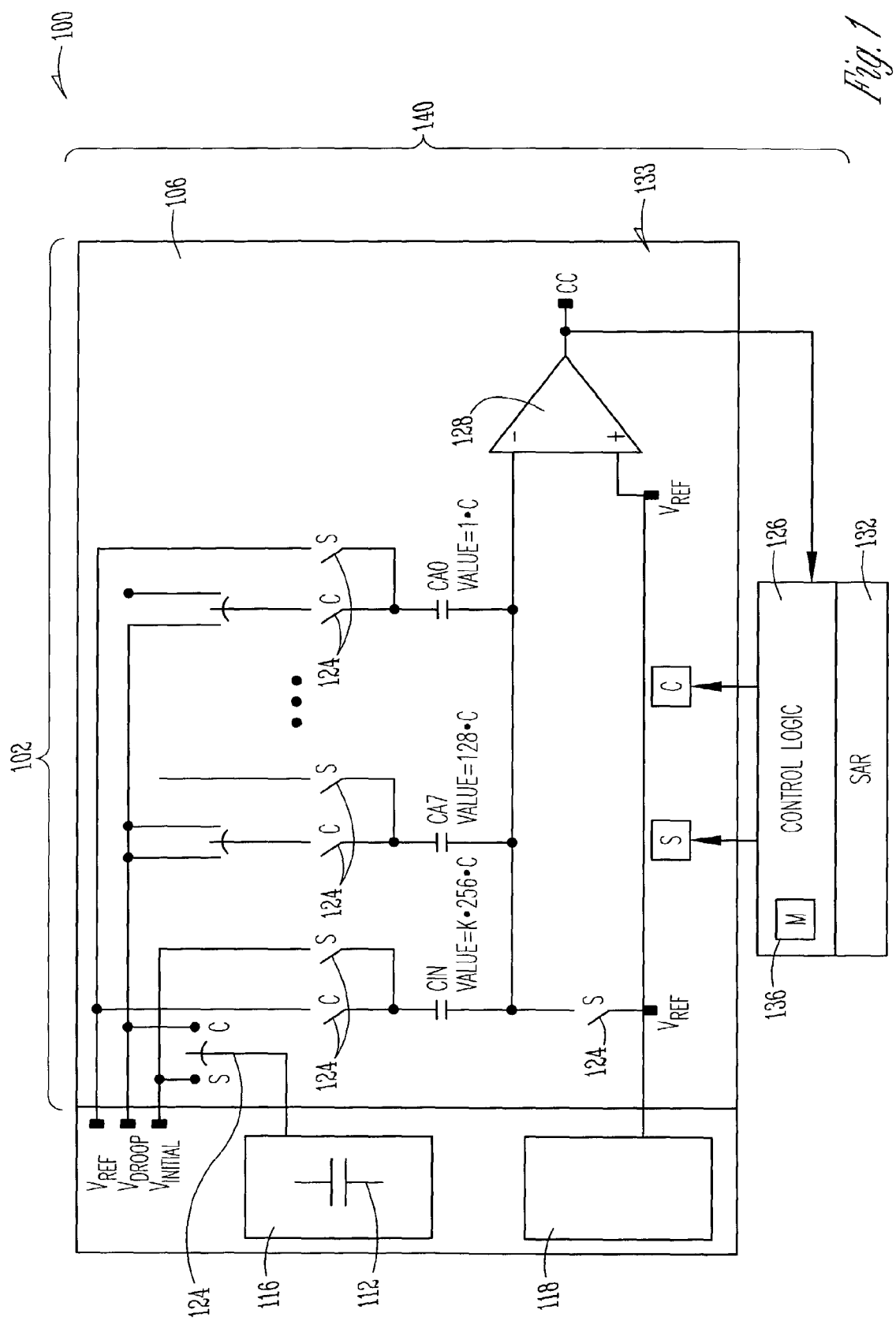
FIG. 1 is a schematic block diagram of an apparatus according to an embodiment of the invention.

In the following detailed description of various embodiments of the invention, information with respect to making and using the various embodiments, including a best mode of practicing such embodiments, is provided. Thus, reference is made to the accompanying drawings which form a part hereof, and in which are shown by way of illustration, and not of limitation, specific embodiments in which the invention may be practiced. In the drawings, like numerals describe substantially similar components throughout the several views. The embodiments illustrated are described in sufficient detail to enable those skilled in the art to practice the teachings disclosed herein. Other embodiments may be utilized and derived therefrom, such that electrical, structural, and logical substitutions and changes may be made without departing from the scope of this disclosure. The following detailed description, therefore, is not to be taken in a limiting sense, and the scope of various embodiments of the invention is defined only by the appended claims, along with the full range of equivalents to which such claims are entitled.

It is understood that the embodiments described herein may relate to ventricular and/or atrial pacing therapy. Such embodiments can be applied to mammalian hearts, human and otherwise. The embodiments also include single chamber and dual chamber applications. It is also understood that the apparatus, systems, and methods provided herein are not limited to implantable devices, and may be used in devices external to the body. Additionally, other devices within and without the area of cardiac rhythm management may employ aspects of the various concepts presented herein without departing from the scope of various embodiments of the invention.

By far, the most popular A/D conversion technique in general use for moderate to high speed applications is the successive-approximation type A/D. This device falls into a class known as feedback type A/D converters, where a D/A converter is in the feedback loop of a digital control circuit which changes its output until it equals the analog input. In the case of the successive-approximation converter, the converter is controlled in an optimum manner to complete a conversion in just n-steps, where n is the resolution of the converter in bits.

The operation of a successive-approximation converter is analogous to weighing an unknown on a laboratory balance scale using standard weights in a binary sequence, for example: 1, ½, ¼, ⅛ . . . 1/n kilograms. This process begins with the largest standard weight and proceeds in order down to the smallest one.

The largest weight is placed on the balance pan first; if it does not tip, the weight is left on and the next largest weight is added. If the balance tips, the weight which caused the balance to tip is removed and the next smaller weight is added. The same procedure is used for the next smaller weight and so on down to the smallest weight. After the nth standard weight has been tried and a decision made, the weighing process is finished. The total of the standard weights remaining on the balance is the closest possible approximation to the unknown.

A/D converters have a conversion voltage range which may extend, for example, from 0.0 V up to a maximum positive input voltage of $V_{range}$. Depending on the resolution of the A/D converter (usually expressed in terms of N bits), this conversion range is divided into $2^N$ parts. For example, an 8-bit A/D converter divides the conversion voltage range into 256 parts, or slots. Thus, an A/D converter takes an input voltage, $V_{in}$, and determines which slot the particular input voltage occupies.

The conversion voltage range of an A/D converter can be fixed, or determined by another signal presented to an input of the A/D converter, $V_{range}$. The output value M of this A/D converter with a dynamic conversion range, as a function of $V_{REF}$, $V_{range}$, and $V_{in}$, can be expressed as follows:

$$M = \begin{cases} 0 & \text{for } V_{in} < V_{REF} \\ \text{INTEGER}[256*(V_{in}-V_{REF})/(V_{range}-V_{REF})] & \text{for } V_{REF} \leq V_{in} < V_{range} \\ 255 & \text{for } V_{in} \geq V_{range} \end{cases}$$

The following definitions apply herein: $V_{pace,initial}$=actual initial pacing voltage; $V_{pace,droop}$=actual pacing droop voltage; $V_{REF}$=arbitrary, stable analog reference voltage, including zero volts, or ground; $V_{INITIAL}$ the referenced pacing voltage=$V_{pace,initial}$+$V_{REF}$; $V_{DROOP}$ the referenced droop voltage=$V_{pace,droop}$+$V_{REF}$.

FIG. 1 is a schematic block diagram of an apparatus according to an embodiment of the invention. The apparatus 100 employs portions of a switched-capacitor successive approximation A/D converter circuit 102 that has a dynamic conversion range, shown as an N=8 bit example, included in the measurement module 106. Here, $V_{INITIAL}$ is a referenced pacing voltage derived from or supplied by, for example, the pacing supply capacitor 112 within a monitored energy source 116. $V_{REF}$ can be, for example, an arbitrary analog reference voltage supplied by a stable, or substantially fixed reference energy source 118. The reference indication, $V_{REF}$, can be any voltage, including zero volts, or ground (of course, as appropriate, those of ordinary skill in the art, after reading this disclosure, will realize that reference current sources may also be used). Thus the referenced initial pacing voltage $V_{INITIAL}$ can be expressed as the actual initial pacing voltage $V_{pace,initial}$+the reference indication $V_{REF}$.

$V_{DROOP}$ is a referenced pacing droop voltage (i.e., the droop voltage during the pace), which can also be derived from or obtained from the monitored energy source 116. Thus the referenced pacing droop voltage $V_{DROOP}$ can be expressed as the actual pacing droop voltage $V_{pace,droop}$+the reference indication $V_{REF}$. By coupling the measurement module 106 the monitored energy source 116 and the reference energy source 118, the referenced initial pacing voltage, $V_{INITIAL}$, can be converted into an N=8 bit unsigned magnitude value, "M", according to the conversion range established by the referenced pacing droop voltage, $V_{DROOP}$.

The "S" and "C" labels next to the switches 124 denote control signals applied by the control logic 126 to activate the switches 124 ("S" for "sample" and "C" for "convert", respectively). During the "Sample" time period, the referenced pacing voltage $V_{INITIAL}$ is sampled onto capacitor $C_{IN}$, while capacitors $C_{A7}$–$C_{A0}$ sample the voltage $V_{REF}$. During the "Convert" time period, the referenced droop voltage $V_{DROOP}$ is used to balance the charge sampled onto capacitor $C_{IN}$ during the "Sample" phase, using the comparator 128. The amount of capacitance provided by a selected combination of capacitors $C_{A7}$–$C_{A0}$ needed to achieve this balance determines the result of the conversion.

Returning to the previous operational explanation of an A/D converter with a dynamic conversion range, and assuming that the reference voltage is zero volts, or ground, it can be understood that the output value of the A/D converter is essentially a function of $V_{in}/V_{range}$. Assuming that the actual initial pacing voltage $V_{pace,initial}$ is substituted for $V_{in}$, and the actual pacing droop voltage $V_{pace,droop}$ is substituted for $V_{range}$, the A/D output value is then a function of $V_{pace,initial}/V_{pace,droop}$. While this function appears to be dependent on the initial pacing voltage $V_{pace,initial}$, it should be noted that the actual pacing droop voltage $V_{pace,droop}$ is also a function of the actual initial pacing voltage $V_{pace,initial}$ as follows:

$$V_{pace,initial} - V_{pace,droop} = V_{pace,initial} * e^{-(tpw/T)}$$

where tpw is the pacing pulse width and T is the time constant of the pacing supply capacitor discharge. Re-arranging the equation yields:

$$V_{pace,droop} = V_{pace,initial} * (1 - e^{-(tPw/T)})$$

such that the ratio of $V_{pace,initial}/V_{pace,droop}$ is seen to be equal to $(1/(1-e^{-(tpw/T)}))$. Thus, the A/D converter output value is a function of $(1/(1-e^{-(tpw/T)}))$, which is independent of the initial pacing voltage.

The resulting 8-bit unsigned digital value, M, now shown to be independent of the actual initial pacing voltage $V_{pace,initial}$, can be stored in a successive approximation register 132 (coupled to or included in the control logic 126). The digital value can be expressed as a function of the referenced values $V_{INITIAL}$ and $V_{DROOP}$ using the following charge-balance expression (N=8 bits corresponds to 256 units of capacitance):

$$256*(V_{INITIAL} - V_{REF}) = M*(V_{DROOP} - V_{REF})$$

Substituting $(V_{pace,initial} + V_{REF})$ for $V_{INITIAL}$, substituting $(V_{pace,droop} + V_{REF})$ for $V_{DROOP}$, and solving for M, provides:

$$M = 256*(V_{pace,initial}/V_{pace,droop}) = 256/(1-e^{-(tpw/T)})$$

Since T=Rout*Cout (i.e., the impedance to be measured multiplied by the output capacitance of the pacing circuit), solving for Rout gives:

$$Rout = -tpw/(Cout \cdot \ln(1-256/M))$$

Thus, a voltage-independent lead impedance measurement is provided by coupling a measurement module, including a sampler (and optionally, an attenuator) circuit to a monitored energy source, such as a droop voltage source and/or amplifier, along with a reference source, such as a reference voltage source, which can provide any voltage, including zero volts, or ground. The sampler/attenuator circuit samples the initial pacing voltage across the pacing supply capacitor prior to delivery of the pacing pulse. A referenced pacing droop voltage is then used to drive the conversion range of an A/D converter, for example, and the droop measurement is normalized to the amplitude of the initial pacing voltage. The normalization process effectively makes the measurement independent of the actual initial pacing voltage. Additionally, the output value from the measurement process does not necessarily depend on the value of $V_{REF}$, since the $V_{INITIAL}$ and $V_{DROOP}$ referenced voltages are assumed to have $V_{REF}$ as a common reference voltage. In practice, the actual initial pacing voltage $V_{pace,initial}$ may need to be attenuated to a level that is within the operating voltage of the sampling circuitry. Therefore K may be used as a scaling factor, typically less than or equal to a value of 1.0, which represents the optional attenuation of the actual initial pacing voltage $V_{pace,initial}$. If the scaling factor K is used, Rout becomes:

$$Rout = -tpw/(Cout \cdot \ln(1 - 256*K/M))$$

Those of ordinary skill in the art, upon reading this disclosure, will realize that the actual pacing droop voltage $V_{pace,droop}$ may also be scaled by any desired amount, as needed.

Figure 2A:
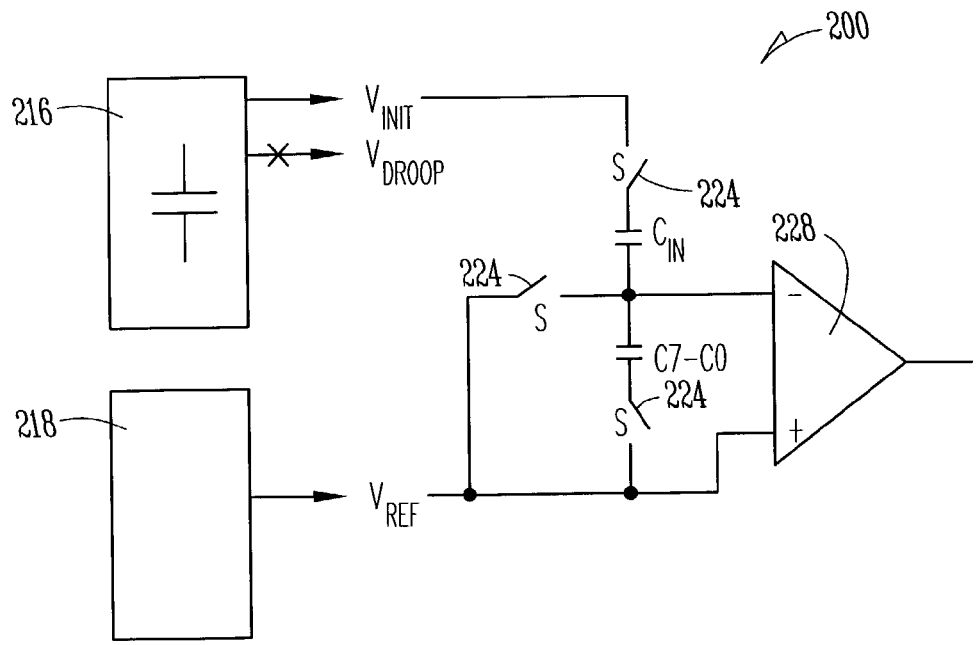
FIGS. 2A and 2B are schematic block diagrams of apparatus according to alternative embodiments of the invention.
Figure 2B:
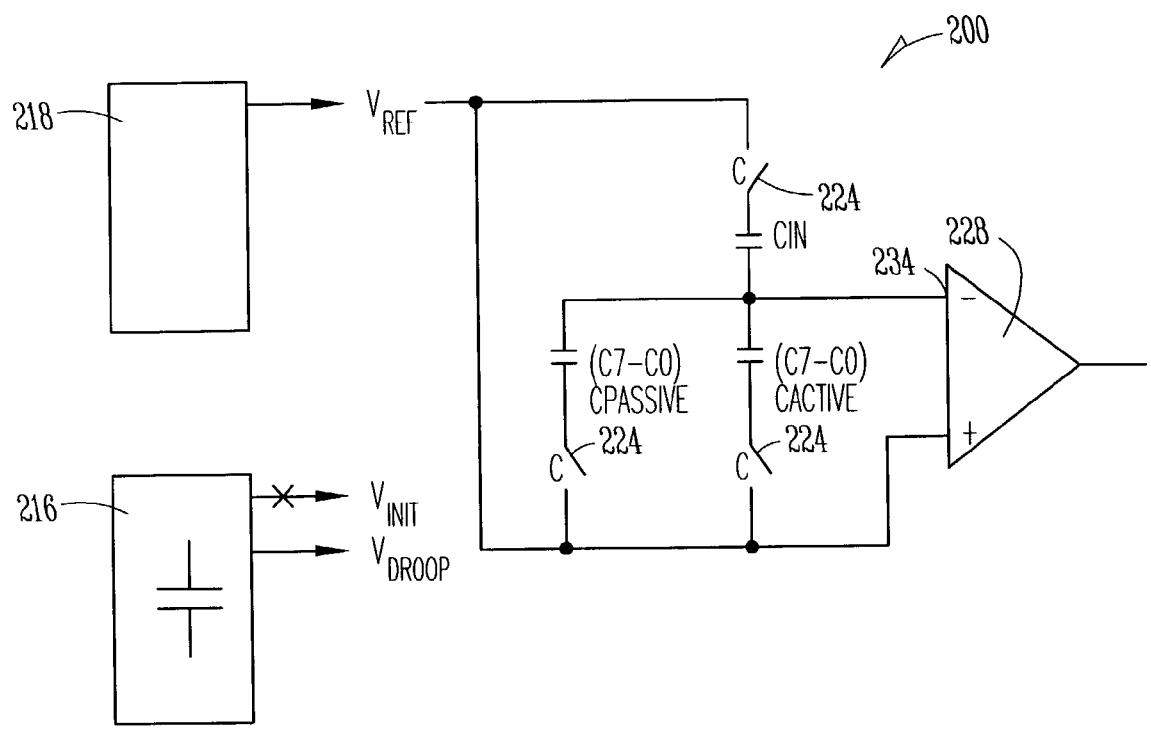

FIGS. 2A and 2B are schematic block diagrams of apparatus according to alternative embodiments of the invention. In this case, the apparatus 200 is shown in each of two states: FIG. 2A illustrates the Sample state of operation, and FIG. 2B illustrates the Convert state of operation.

In FIG. 2A, the switches 224 in the "S" position are used to sample the referenced pacing voltage $V_{INITIAL}$ provided by, or derived from the monitored energy source 216 (the reference voltage $V_{REF}$ is provided by the reference energy source 218). Thus, it is actually the referenced voltage $V_{INITIAL}$ that is sampled onto the capacitor $C_{IN}$, and presented at the minus input 234 of the comparator 228 during the Convert state of operation.

In FIG. 2B, the switches 224 in the "C" position are used to balance some portion of the charge accumulated on the capacitor $C_{IN}$ during the Sample state against the referenced droop voltage $V_{DROOP}$. At the end of the process, a subset of the capacitors $C_{A7}$–$C_{A0}$ (e.g., a first subset, or $C_{ACTIVE}$) will have accumulated a charge equal to that which exists on the capacitor $C_{IN}$ and the input node 234 will be at a value of approximately $V_{REF}$. Thus, if M is the decimal 8-bit conversion value result, the charge on $C_{ACTIVE}$=M/255 times the charge on $CA_7$–$C_{A0}$, and the charge on the remaining capacitors (e.g., a second subset of the capacitors $C_{A7}$–$C_{A0}$, or $C_{PASSIVE}$)=(255−M)/255.

It should be noted that voltage sources, capacitors, and voltages have been used to illustrate specific embodiments of the invention. However, other embodiments may use current sources, combinations of voltage and current sources, inductors and other energy storage devices, such as batteries, and currents and combinations of voltages and currents to arrive at the same result, which is measurement that is substantially independent of the initial pacing voltage $V_{pace,initial}$, as well as the reference indication, $V_{REF}$.

The reference energy source 118, 218 should provide a substantially stable or fixed amount of voltage and/or current for use as a reference indication to the apparatus 100, 200, and as indicated above, the reference provided may be zero volts, or ground. The particular amount of the reference indication may be approximately 0.5 volts, 1.0 volts, or 1 milliampere, or any other arbitrary value, as long as the presented value is relatively stable, such as varying less than about 0.1% per minute.

Thus it is understood that an apparatus 100, 200 according to various embodiments of the invention includes a measurement module 106 coupled to a monitored energy source 116, 216 and a reference energy source 118, 218. The monitored energy source 116, 216 provides a first indication (e.g., a voltage or a current) associated with an actual initial pacing voltage and a second indication (e.g., a voltage or a current) associated with an actual pacing droop voltage. The monitored energy source 116, 216 may include a pacing supply capacitor 112. The reference energy source 118, 218 provides a common, relatively stable reference indication (e.g., a voltage or a current). The measurement module 106 then provides a third indication (e.g., a voltage, a current, or a value, such as a numerical value) associated with a ratio of the actual initial pacing voltage and the actual pacing droop voltage, or values derived therefrom, wherein the ratio is substantially independent of the actual initial pacing voltage.

The measurement module 106 may in turn include a sampler 102 and a converter 126. The sampler 102 and converter 126 can be included as portions of a successive approximation A/D converter 133, for example. The sampler 102 can be used to sample the referenced pacing voltage $V_{INITIAL}$ (i.e., $V_{pace,initial}+V_{REF}$) and the referenced pacing droop voltage $V_{DROOP}$ (i.e., $V_{pace,droop}+V_{REF}$). The converter 126, coupled to the sampler 102, is capable of generating the third indication, derived from the ratio of $V_{pace,initial}$ to $V_{pace,droop}$, which may be stored in a successive approximation register included in the A/D converter 133.

Several specific selections can be made with respect to the design of various embodiments of the invention. For example, the first indication can be selected so as to be substantially equal to the actual initial pacing voltage $V_{pace,initial}$, or alternatively, to the referenced initial pacing voltage $V_{INITIAL}$. The second indication can be selected so as to be substantially equal to the actual pacing droop voltage $V_{pace,droop}$, or alternatively, to the referenced pacing droop voltage $V_{DROOP}$. The reference indication can be selected so as to be substantially equal to an arbitrary reference indication, such as a reference voltage $V_{REF}$, or alternatively, to zero volts and/or ground.

Figure 3:
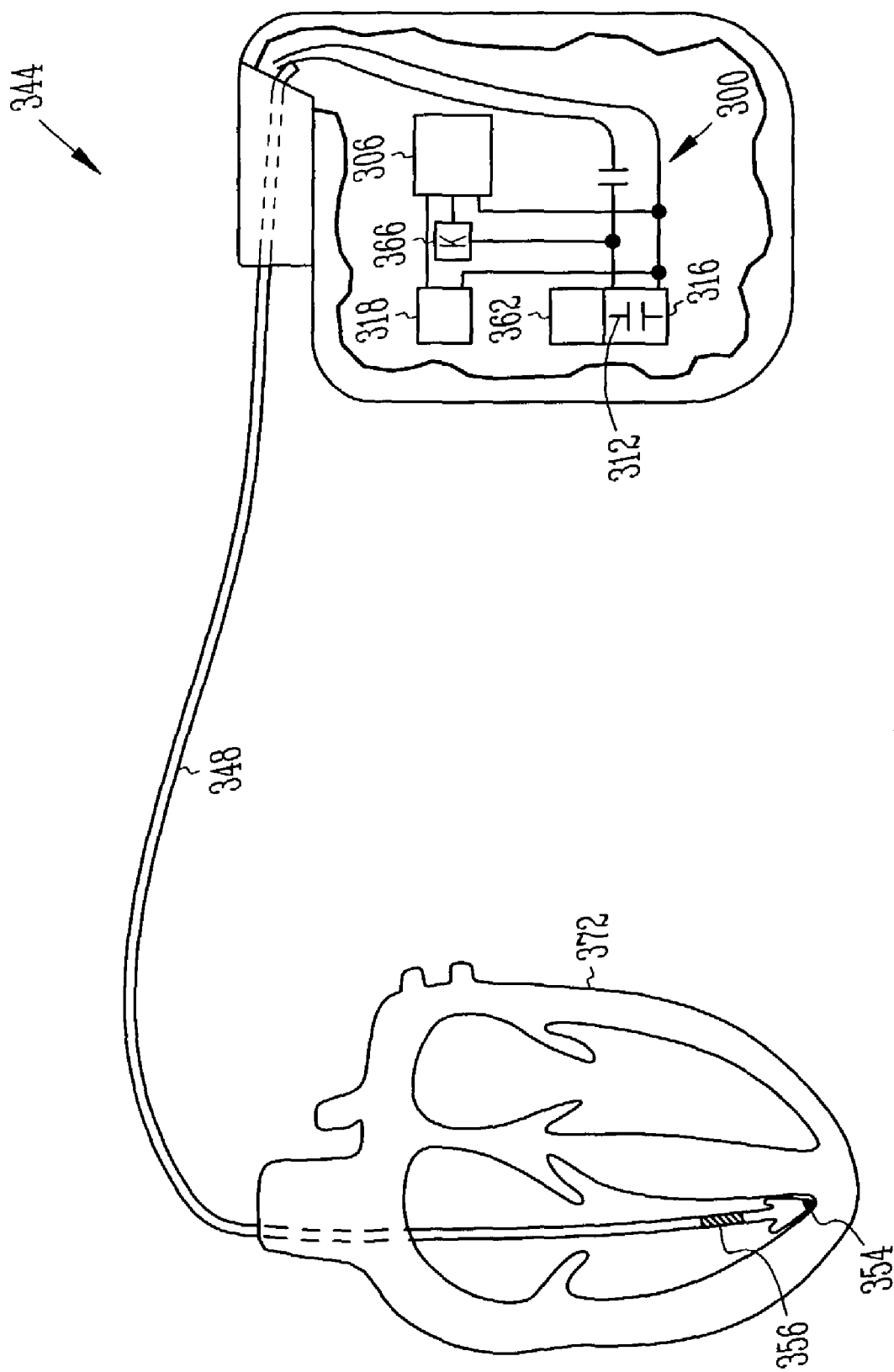
FIG. 3 is a schematic block diagram of a system according to an embodiment of the invention.

FIG. 3 is a schematic block diagram of a system according to an embodiment of the invention. Here a system 344, such as a cardiac rhythm management system, is shown which includes an apparatus 300 which is similar to or identical to that depicted in FIGS. 1 (i.e., element 100), 2A, and 2B (i.e., element 200). Thus, the apparatus 300 includes a measurement module 306 coupled to a monitored energy source 316 and a reference energy source 318. The monitored energy source 316 may include a pacing voltage generator 362 coupled to a pacing supply capacitor 312. The reference energy source 318 can be selected so as to provide a reference indication, such as a substantially fixed voltage output value $V_{REF}$, for example.

As mentioned previously, an attenuator 366 can be electrically coupled between the monitored energy source 316 and the measurement module 306. The attenuator is capable of attenuating the magnitude associated with the actual initial pacing amplitude voltage $V_{pace,initial}$ by a factor of K≦about 1.0. Also, as described above, the system 344 may include a plurality of capacitors (e.g, capacitors $C_{A7}-C_{A0}$ forming part of the sampler 102 in FIG. 1) arranged in a successive approximation sampling configuration as part of the measurement module 306, as well as control logic (e.g., element 126 in FIG. 1) coupled to the capacitors.

The measurement module 306 included in the apparatus 300 is electronically coupled to a lead wire 348, which is in turn coupled to tip and ring electrodes 354, 356, respectively. The lead wire 348 is used to couple the system 344 to the heart 372. In this case, the third indication provided by the system 344 may be selected so as to be approximately proportional to an impedance associated with at least one of the electrodes 354, 356 coupled to the lead wire 348. It should be understood, therefore, that the impedance may include not only the impedance of the lead wire 348, but also the impedance of the tissue and fluids in and around the heart 372 which may be located between the electrodes 354, 356.

The apparatus 100, 200, 300, the switched-capacitor or sampler circuit 102, the measurement module 106, the monitored energy source 116, 216, the reference energy source 118, 218, the control logic 126, the successive approximation register 132, the comparator 128, 228, and the A/D converter 133 may all be characterized as "modules" herein. Such modules may include hardware circuitry, and/or a processor and/or memory circuits, software program modules, and/or firmware, and combinations thereof, as desired by the architect of the apparatus 100, 200, 300, and the system 344, and as appropriate for particular implementations of various embodiments of the invention.

One of ordinary skill in the art will understand that the apparatus and systems of the present invention can be used in applications other than for successive approximation conversion, and other than for systems which include cardiac rhythm management systems, and thus, the invention is not to be so limited. The illustrations of an apparatus 100, 200, 300, and a system 348 are intended to provide a general understanding of the structure of the present invention, and they are not intended to serve as a complete description of all the elements and features of apparatus and systems that might make use of the structures described herein.

Applications that may include the novel apparatus and systems of the present invention include electronic circuitry used in communication and signal processing circuitry, modems, processor modules, embedded processors, and application-specific modules, including multilayer, multichip modules. Such apparatus and systems may further be utilized as sub-components within a variety of electronic systems, including cellular telephones, personal computers, radios, and others.

Figure 4:
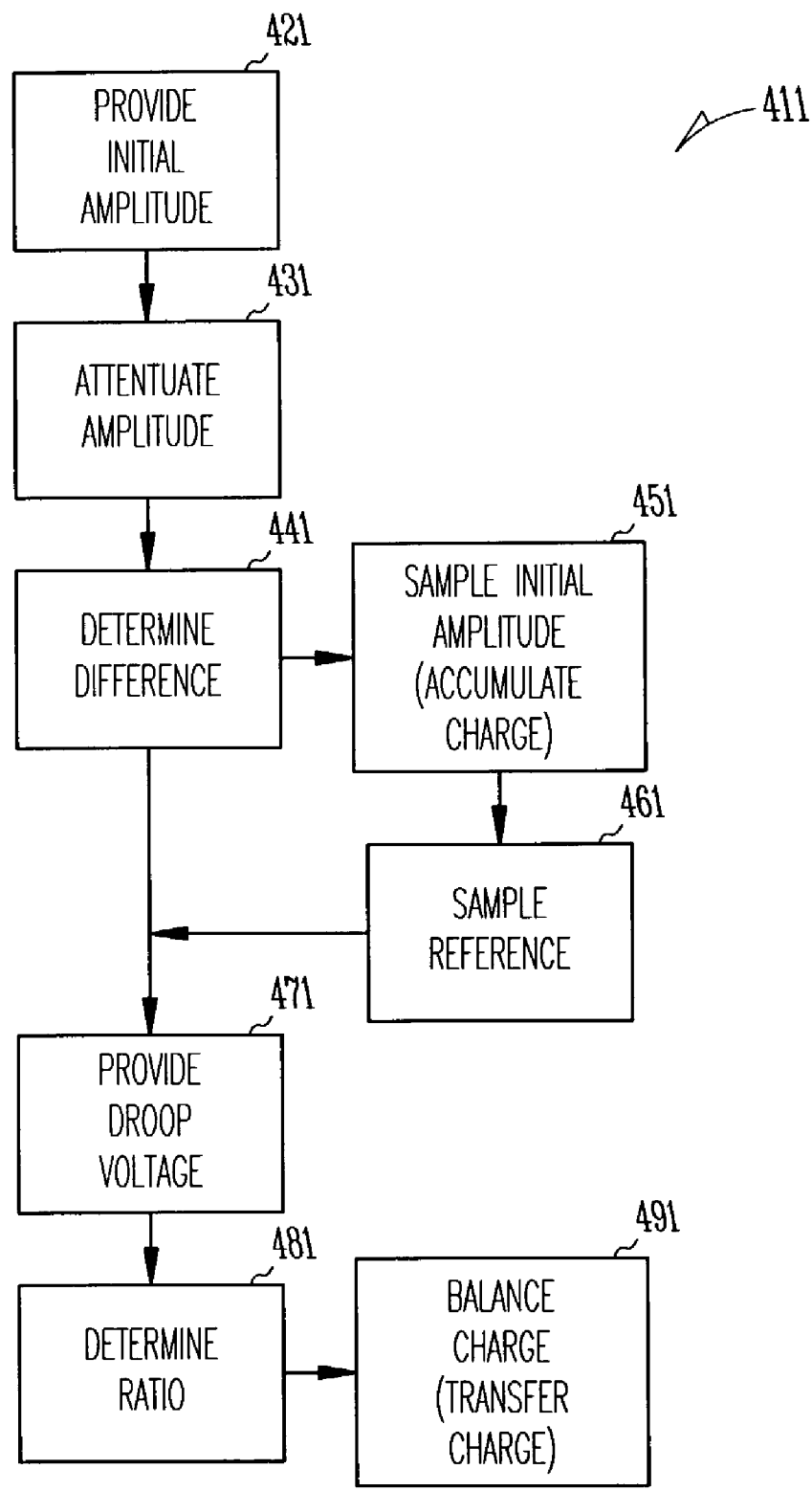
FIG. 4 is a flow diagram illustrating a method of measuring impedance according to an embodiment of the invention.

FIG. 4 is a flow diagram illustrating a method of measuring impedance according to an embodiment of the invention. The method 411 may begin by providing an actual initial pacing voltage, for example, across a pacing supply capacitor at block 421. Of course, instead of providing the actual initial pacing voltage, the method may include providing a current or some other value selected to be approximately proportional to the actual initial pacing voltage instead. The method may continue with attenuating the actual initial pacing voltage (e.g., $K^*V_{pace,initial}$), or the selected approximate proportional value, if necessary, at block 431. The method may continue with providing an actual pacing droop voltage, or a current or some other value selected to be approximately proportional to the actual pacing droop voltage, at block 441. As is the case with the actual initial pacing voltage, the method may continue with attenuating the actual pacing droop voltage (e.g., $K^*V_{pace,droop}$), or the selected approximate proportional value, if necessary, at block 445.

The actual initial pacing voltage $V_{pace,initial}$ (or some value selected to be approximately proportional to the actual initial pacing voltage) and the actual pacing droop voltage $V_{pace,droop}$ (or some value selected to be approximately proportional to the actual pacing droop voltage) may then be used to provide referenced voltages, such as $V_{INITIAL}$ and $V_{DROOP}$ (or other values proportional to such reference voltages) at block 451. Thus, for example, by providing a reference indication, such as a voltage $V_{REF}$ (an arbitrary, stable analog reference voltage), including zero volts, or ground; $V_{INITIAL}$, the referenced pacing voltage, may be obtained by determining $V_{pace,initial}+V_{REF}$; and $V_{DROOP}$, the referenced droop voltage, may be obtained by determining $V_{pace,droop}+V_{REF}$. Of course, if other proportional values are desired, instead of voltages, other types of references, such as current references, may be used.

The method may continue at block 461 with determining a ratio substantially independent of the reference indication, which can be selected so as to be approximately proportional to the quotient, or ratio, of the actual initial pacing voltage to the actual pacing droop voltage.

Determining the ratio at block 461 may include accumulating a charge at block 471, via sampling, and balancing the charge sampled onto a reference capacitor against a charge sampled onto a plurality of other capacitors at block 481. Accumulating a charge at block 471 may include sampling a first amplitude value selected so as to be proportional to the actual initial pacing voltage, and then sampling a second amplitude value selected so as to be proportional to the reference indication. Of course, the first amplitude value may be selected so as to be approximately equal to the actual initial pacing voltage, and the second amplitude value may be selected so as to be approximately equal to the reference indication, if desired. Sampling the first amplitude value may include sampling the actual initial pacing voltage using a plurality of capacitors arranged in a successive approximation sampling configuration, as described above. Sampling the second amplitude value may include sampling a substantially fixed voltage or current value provided by the reference energy source. The method may conclude by determining an output value, such as an impedance or resistance, substantially independent of the reference indication (e.g., Rout, as described previously).

Referring to the methods just described, it should be clear that some embodiments of the present invention may also be realized in the context of computer-executable instructions, such as program modules, being executed by a computer. Generally, program modules may include routines, programs, objects, components, data structures, etc. that perform particular tasks or implement particular abstract data types. As such, any of the modules 100, 102, 106, 116, 118, 126, 128, 132, 133, 200, 216, 218, 228, and 300 described herein may include software operative on one or more processors to perform methods according to the teachings of various embodiments of the present invention.

One of ordinary skill in the art will understand, upon reading and comprehending this disclosure, the manner in which a software program can be launched from a computer readable medium in a computer-based system to execute the functions defined in the software program. One of ordinary skill in the art will further understand the various programming languages that may be employed to create one or more software programs designed to implement and perform the methods disclosed herein. The programs can be structured in an object-orientated format using an object-oriented language such as Java, Smalltalk, or C++. Alternatively, the programs can be structured in a procedure-orientated format using a procedural language, such as COBOL or C. The software components may communicate using any of a number of mechanisms that are well-known to those skilled in the art, such as application program interfaces (API) or interprocess communication techniques such as the Remote Procedure Call (RPC). However, the teachings of various embodiments of the present invention are not limited to any particular programming language or environment.

As is evident from the preceding description, and referring back to FIG. 1, it can be seen that during the operation of the apparatus 100 (as well as apparatus 200 and 300 in FIGS. 2A, 2B and 3, respectively), a processor or control logic 126 may access some form of computer-readable media, such as memory 136. Thus, a system 344 having an apparatus 300 according to an embodiment of the invention may also include a processor 132 coupled to a memory 136, volatile (e.g., Random Access Memory) or nonvolatile (e.g., a flash memory).

By way of example and not limitation, computer-readable media may comprise computer storage media and communications media. Computer storage media includes volatile and non-volatile, removable and non-removable media implemented in any method or technology for storage of information such as computer-readable instructions, data structures, program modules or other data. Communications media specifically embodies computer-readable instructions, data structures, program modules or other data in a modulated data signal such as a carrier wave, coded information signal, and/or other transport mechanism, which includes any information delivery media. The term "modulated data signal" means a signal that has one or more of its characteristics set or changed in such a manner as to encode information in the signal. By way of example and not limitation, communications media also includes wired media such as a wired network or direct-wired connections, and wireless media such as acoustic, optical, radio frequency, infrared and other wireless media. Combinations of any of the above are also included within the scope of computer-readable and/or accessible media.

Thus, it is now easily understood that another embodiment of the invention may include an article 140 comprising a machine-accessible medium or memory 136 having associated data, wherein the data, when accessed, results in a machine (e.g. a processor or control logic 126) performing activities such as determining a ratio approximately proportional to the sum of an actual initial pacing amplitude voltage and a reference indication, and the sum of an actual droop pacing voltage and the reference indication. The ratio should then be substantially independent of the reference indication (e.g., the ratio of a referenced pacing voltage to a referenced droop voltage). Other activities may include providing an initial pacing amplitude voltage and/or a droop voltage across a pacing supply capacitor. Still other activities may include accumulating a charge on a reference capacitor proportional to a sum of the initial pacing amplitude voltage and the reference indication, and then transferring the charge on the reference capacitor to at least one other capacitor (e.g., a plurality of sampling capacitors, such as capacitors $CA_7$–$C_{40}$ shown in FIG. 1).

It is contemplated that various embodiments of the invention are capable of operating in conjunction with a variable-gain droop amplifier, such that attenuation of the resulting voltage before sampling is unnecessary. Alternatively, attenuation may be used to accommodate apparatus and systems which utilize a fixed-gain droop amplifier.

Although specific embodiments have been illustrated and described herein, those of ordinary skill in the art will appreciate that any arrangement which is calculated to achieve the same purpose may be substituted for the specific embodiments shown. For example, some embodiments of the invention may be described as a method comprising determining an actual initial pacing voltage, determining an actual pacing droop voltage, and determining a ratio of the actual initial pacing voltage to the actual pacing droop voltage by balancing accumulated charges, wherein the ratio is substantially independent of a reference indication. Thus, this disclosure is intended to cover any and all adaptations or variations of various embodiments of the present invention. It is to be understood that the above Detailed Description has been made in an illustrative fashion, and not a restrictive one. Combinations of the above embodiments, and other embodiments not specifically described herein will be apparent to those of skill in the art upon reviewing the above description. The scope of various embodiments of the invention includes any other applications in which the above structures and methods are used. Therefore, the scope of various embodiments of the invention should be determined with reference to the appended claims, along with the full range of equivalents to which such claims are entitled.

It is emphasized that the Abstract is provided to comply with 37 C.F.R. §1.72(b) requiring an abstract that will allow the reader to quickly ascertain the nature of the technical disclosure. It is submitted with the understanding that it will not be used to interpret or limit the scope or meaning of the claims. It should also be noted that in the foregoing Detailed Description, various features may be grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment.

What is claimed is:

1. A cardiac measurement apparatus, comprising:
a monitored energy source providing a first indication associated with an actual initial pacing voltage and a second indication associated with a actual pacing droop voltage;
a reference energy source to provide a reference indication; and
a measurement module coupled to the monitored energy source and the reference energy source, the measurement module to provide a third indication associated with a ratio of the first indication and the second indication, the ratio being substantially independent of the reference indication, wherein the measurement module comprises a sampler to sample a sum of the first indication and the reference indication and a converter coupled to the sampler, the converter to generate the third indication derived from the sum, and wherein the sampler and the converter are included in a successive approximation analog to digital converter.

2. The apparatus of claim 1, wherein the third indication is stored in a successive approximation register included in the analog to digital converter.

3. A cardiac measurement system, comprising:
an apparatus, including a monitored energy source providing a first indication associated with an actual initial pacing voltage and a second indication associated with an actual pacing droop voltage, a reference energy source to provide a reference indication value, and a measurement module coupled to the monitored energy source and the reference energy source, the measurement module to provide a third indication associated with a ratio of the first indication and the second indication, the ratio being substantially independent of the reference indication;
a lead wire electrically coupled to the measurement module; and
an attenuator electrically coupled between the monitored energy source and the measurement module, wherein the attenuator is capable of attenuating a magnitude associated with the actual initial pacing voltage by a factor of $K \leq 1.0$.

4. A cardiac measurement method, comprising:
determining a first sum of an actual initial pacing voltage and a reference indication;
determining a second sum of an actual pacing droop voltage and the reference indication;
determining a ratio of the first sum and the second sum which is substantially independent of the reference indication; and
attenuating a value associated with the actual initial pacing voltage.

5. A cardiac measurement apparatus, comprising:
a monitored energy source providing a first indication associated with an actual initial pacing voltage and a second indication associated with a actual pacing droop voltage;
a reference energy source to provide a reference indication;
a measurement module coupled to the monitored energy source and the reference energy source, the measurement module to provide a third indication associated with a ratio of the first indication and the second indication, the ratio being substantially independent of the reference indication; and
a successive approximation analog to digital converter to store the third indication derived from a sampled sum of the first indication and the reference indication.

6. The apparatus of claim 5, wherein the first indication is substantially equal to the actual initial pacing voltage, wherein the second indication is substantially equal to the actual pacing droop voltage, and wherein the reference indication is substantially equal to a reference voltage.

7. The apparatus of claim 5, wherein the monitored energy source comprises:
a pacing supply capacitor.

8. The apparatus of claim 5, wherein the monitored energy source comprises:
a pacing voltage generator.

9. The apparatus of claim 5, wherein the third indication is approximately proportional to an impedance associated with at least one of a plurality of electrodes coupled to a lead wire.

10. The apparatus of claim 5, further comprising:
an attenuator electrically coupled between the monitored energy source and the measurement module, wherein the attenuator is capable of attenuating a magnitude associated with the actual initial pacing voltage by a factor of $K \leq 1.0$.

11. A cardiac measurement method, comprising:
determining a first sum of an actual initial pacing voltage and a reference indication;
storing a sampled version of the first sum in a successive approximation analog-to-digital converter;
determining a second sum of an actual pacing droop voltage and the reference indication; and determining a ratio of the first sum and the second sum which is substantially independent of the reference indication.

12. The method of claim 11, wherein determining a first sum of an actual initial pacing voltage and a reference indication comprises:
    sampling a first amplitude value proportional to the actual initial pacing voltage; and
    sampling a second amplitude value proportional to the reference indication.

13. The method of claim 11, wherein sampling a second amplitude value proportional to the reference indication comprises:
    sampling a substantially fixed voltage value provided by a reference energy source.

14. The method of claim 11, wherein determining a ratio of the first sum and the second sum which is substantially independent of the reference indication comprises:
    balancing a charge sampled onto a reference capacitor against a charge sampled onto a plurality of other capacitors.

15. The method of claim 11, wherein determining a first sum of an actual initial pacing voltage and a reference indication comprises:
    accumulating a charge on a reference capacitor proportional to a sum of the actual initial pacing voltage and the reference indication.

16. The method of claim 11, wherein determining a ratio of the first sum and the second sum which is substantially independent of the reference indication comprises:
    transferring the charge on a reference capacitor proportional to the sum of the actual initial pacing voltage and the reference indication to at least one other capacitor.

* * * * *